United States Patent
Berner et al.

(10) Patent No.: US 7,438,927 B2
(45) Date of Patent: Oct. 21, 2008

(54) METHODS OF TREATMENT USING A GASTRIC RETAINED GABAPENTIN DOSAGE

(75) Inventors: Bret Berner, El Granada, CA (US); Sui Yuen Eddie Hou, Foster City, CA (US); Gloria M. Gusler, Cupertino, CA (US)

(73) Assignee: Depomed, Inc., Menlo Park, CA (US)

( * ) Notice: Subject to any disclaimer, the term of this patent is extended or adjusted under 35 U.S.C. 154(b) by 489 days.

(21) Appl. No.: 10/280,309

(22) Filed: Oct. 25, 2002

(65) Prior Publication Data
US 2003/0100611 A1 May 29, 2003

(51) Int. Cl.
*A61K 9/24* (2006.01)
*A61K 9/20* (2006.01)
*A61K 9/22* (2006.01)
*A61K 9/14* (2006.01)

(52) U.S. Cl. .................. 424/473; 424/464; 424/472; 424/489

(58) Field of Classification Search .................. 424/464, 424/468, 474, 480
See application file for complete search history.

(56) References Cited

U.S. PATENT DOCUMENTS

| | | | |
|---|---|---|---|
| 4,024,175 A | 5/1977 | Satzinger et al. | |
| 4,087,544 A | 5/1978 | Satzinger et al. | |
| 4,152,326 A | 5/1979 | Hartenstein et al. | |
| 4,894,476 A | 1/1990 | Butler et al. | |
| 4,996,058 A | 2/1991 | Sinnreich et al. | |
| 5,007,790 A | 4/1991 | Shell | |
| 5,084,479 A | 1/1992 | Woodruff | |
| 5,582,837 A | 12/1996 | Shell | |
| 5,872,984 A | 2/1999 | Berglund et al. | |
| 5,906,832 A * | 5/1999 | Jao et al. | 424/465 |
| 5,972,389 A * | 10/1999 | Shell et al. | 424/501 |
| 6,054,482 A | 4/2000 | Augart et al. | |
| 6,120,803 A * | 9/2000 | Wong et al. | 424/473 |
| 6,162,466 A | 12/2000 | Licht et al. | |
| 6,255,526 B1 | 7/2001 | Pesachovich et al. | |
| 6,294,690 B1 | 9/2001 | Deering et al. | |
| 6,310,098 B1 | 10/2001 | Guttuso, Jr. | |
| 6,333,352 B1 * | 12/2001 | Derakhshan | 514/557 |

(Continued)

FOREIGN PATENT DOCUMENTS

EP     0 458 751 A1    5/1991

(Continued)

OTHER PUBLICATIONS

Davis et al., "Relationship between the rate of appearance of oxprenolol in the systemic circulation and the location of an oxprenolol Oros 16/260 drug delivery system within the gastrointestinal tract as determined by scintigraphy," Br. J. Clin. Pharmac. (1988) 26:435-443.

(Continued)

*Primary Examiner*—Humera N Sheikh
(74) *Attorney, Agent, or Firm*—Paul B. Simboli; Judy M Mohr; King & Spalding LLP

(57) ABSTRACT

A method of treatment for epilepsy and other disease states is described, which comprises the delivery of gabapentin in a gastric retained dosage form.

67 Claims, 2 Drawing Sheets

Gabapentin GR Dissolution

U.S. PATENT DOCUMENTS

| | | | |
|---|---|---|---|
| 6,340,475 | B2 | 1/2002 | Shell et al. |
| 6,451,808 | B1 | 9/2002 | Cowles |
| 6,488,962 | B1 | 12/2002 | Berner et al. |
| 6,635,281 | B2* | 10/2003 | Wong et al. .......... 424/473 |
| 2001/0043946 | A1 | 11/2001 | Vilkov |
| 2002/0012679 | A1 | 1/2002 | Bruna et al. |
| 2003/0031711 | A1 | 2/2003 | Fara et al. |
| 2003/0100611 | A1 | 5/2003 | Berner et al. |
| 2003/0104053 | A1 | 6/2003 | Gusler et al. |
| 2005/0064036 | A1 | 3/2005 | Berner et al. |
| 2006/0159743 | A1 | 7/2006 | Berner et al. |

FOREIGN PATENT DOCUMENTS

| | | |
|---|---|---|
| EP | 1 118 321 A1 | 7/2001 |
| WO | WO 01/13894 A1 | 3/2001 |
| WO | WO 01/97612 A1 | 12/2001 |
| WO | WO 01/97782 A1 | 12/2001 |
| WO | WO 03/002151 A1 | 1/2003 |

OTHER PUBLICATIONS

Fix, "Oral drug delivery, small intestine and colon," in Controlled Drug Delivery, Mathiowitz, ed., Wiley & Sons, Inc., 1999, pp. 699-700.

Grundy and Foster, "The nifedipine gastrointestinal therapeutic system (GITS). Evaluation of pharmaceutical, pharmacokinetic and pharmacological properties," Clin. Pharmacokinet. (1988) 26:435-443.

Rocci et al., "Food-induced gastric retention and absorption of sustained -release procainamide," Clin. Pharmacol. Ther. (1987) 42:45-49.

Stevenson et al., "Colonic absorption of antiepileptic agents," Epilepsia (1997) 38:63-67.

Welling and Barbhaiya, "Influence of food and fluid volume on chlorothiazide bioavailability: comparison of plasma and urinary excretion methods," J. Pharm. Sci. (1982) 71:32-35.

Wilding et al., "Relationship between systemic drug absorption and gastrointestinal transit after the simultaneous oral administration of carbamazepine as a controlled-release system and as a suspension of $^{15}$N-labelled drug to healthy volunteers," Br. J. Clin. Pharmac. (1991) 32:573-579.

Bennett et al. (2004) "Gabapentin in the treatment of neurophathic pain" Palliative Med., 18(1):5-11.

Richter et al. (Nov. 2005) "Pregabalin or morphine and gabapentin for neuropathic pain" Expert Op. on Pharmacotherapy, 6(14):2535-2539.

Wesche et al. (Mar. 2005) "A pharmacokinetic comparison of pregabalin and gabapentin" J. of Pain, 6(3), abstract only.

NDA 20-235 (U.S. Food and Drug Administration application No. 020235).

NDA 20-882 (U.S. Food and Drug Administration application No. 020882).

NDA 21-129 (U.S. Food and Drug Administration application No. 021129).

Laird et al. (Jun. 2000) "Use of gabapentin in the treatment of neuropathic pain" Ann. Pharmacotherapy, 34:802-807.

Goa et al. (1993) "Gabapentin: a review of its pharmacological properties and clinical potential in epilepsy" Drugs 46(3):409-427.

Wheeler, G. (2002) "Gabapentin" Curr. Op. Invest. Drugs, 3(3):470-477.

Benetello et al. (1997) "Oral gabapentin disposition in patients with epilepsy after a high-protein meal" Epilepsia, 38(10):1140-1142.

Piyapolrungroj et al. (2001) "Mucosal uptake of gabapentin (neurontin) vs. pregabalin in the small intestine" Pharm. Res. 18(8):1126-1130.

Bennett et al. (Aug. 2000) "Future directions in the management of pain by intraspinal drug delivery" J. Pain and Symptom Management, 20(2):S44-S50.

Stevenson et al. (Aug. 1997) "Contrasting nutrient effects on the plasma level of an amino acid-like antiepileptic agent from jejunal administration in dogs" J. Pharm. Sci. 86(8):953-957.

Solaro et al. (2000) "Gabapentin is effective in treating nocturnal painful spasms in multiple sclerosis" Multiple Sclerosis, 6:192-193.

U.S. Appl. No. 09/425,491, Shell John W. et al.
U.S. Appl. No. 10/029,134, Berner et al.
U.S. Appl. No. 10/014,750, Berner et al.
U.S. Appl. No. 10/045,816, Berner et al.
U.S. Appl. No. 10/024,932, Berner et al.
U.S. Appl. No. 10/066,146, Lim et al.
U.S. Appl. No. 10/045,823, Shell et al.
U.S. Appl. No. 10/213,823, Berner et al.
U.S. Appl. No. 10/235,076, Markey et al.
U.S. Appl. No. 10/281,284, Berner et al.
U.S. Appl. No. 10/293,217, Berner et al.

Andrews et al., "Gabapentin: a New Agent for the Management of Epilepsy," Annals of Pharmacotherapy 28:1188-1196 (1994).

Asconapé et al., "Myoclonus Associated with the Use of Gabapentin," Epilepsia: 41(4):479-481 (2000).

Backonja et al., "Gabapentin for the Symptomatic Treatment of Painful Neuropathy in Patients with Diabetes Mellitus," JAMA 280(21): 1831-1836 (1998).

Bebin et al., "New Anticonvulsant Drugs: Focus on Flunarizine, Fosphenytoin, Midazolam, and Stiripentol," Drugs 48(2): 153-171 (1994).

Benedetti, "Enzyme Induction and Inhibition by New Antiepileptic Drugs: a Review of Human Studies," Fundam. Clin. Pharmacol. 14: 301-319 (2000).

Ben-Menachem, "New Antiepileptic Drugs and Non-pharmacological Treatments," Current Opinion in Neurology, 13: 165-170 (2000).

Bennett et al., "Future Directions in the Management of Pain by Intraspinal Drug Delivery," Journal of Pain and Symptom Management 20(2): S44-250 (Aug. 2000).

Bernus et al., "Anticonvulsant Therapy in Aged Patients: Clinical Pharmacokinetic Considerations," Drugs & Aging 10(4): 278-289 (1997).

Beydoun, "Monotherapy Trials of New Antiepileptic Drugs," Epilepsia 38 (Suppl. 9): S21-S31 (1997).

Bialer, "Comparative Pharmacokinetics of the Newer Antiepileptic Drugs," Clinical Pharmacokinetics 24(6): 441-452 (1993).

Blum et al., "Pharmacokinetics of Gabapentin in Subject with Various Degrees of Renal Function," Clinical Pharmacology and Therapeutics 56(2): 154-159 (1994).

Bourgeois, "New Antiepileptic Drugs," Arch Neurol. 55: 1181-1183 (1998).

Bourgeois, "Important Pharmacokinetic Properties of Antiepileptic Drugs," Epilepsia 36(Suppl. 5): S1-S7 (1995).

Bourgeois, "Pharmacokinetic Properties of Current Antiepileptic Drugs: What Improvements are Needed?" Neurology 55 (Suppl 3): S11-S16 (2000).

Boyd et al., "Clinical Research: Effects of Age and Gender on Single-Dose Pharmacokinetics of Gabapentin," Epilepsia 40(4): 474-479 (1999).

Brown et al., "Cloning and Deletion Mutagenesis of the $\alpha_2\delta$ Calcium Channel Subunit from Porcine Cerebral Cortex," Journal of Biological Chemistry 273(39): 25458-25465 (1998).

Browne, "Long-Term Efficacy and Toxicity of Gabapentin," Neurology 43: A307 (1993) (578P).

Chadwick, "Gabapentin," Lancet 343(Jan. 8): 89-91 (1994).

Chadwick, "An Overview of the Efficacy and Tolerability of New Antiepileptic Drugs," Epilepsia 38 (Suppl. 1): S59-S62 (1997).

Chadwick et al., "Clinical Administration of New Antiepileptic Drugs: An Overview of Safety and Efficacy," Epilepsia 37 (Suppl. 6): S17-S22 (1996).

Cramer et al., "New Antiepileptic Drugs: Comparison of Key Clinical Trials," Epilepsia 40(5): 590-600 (1999).

Curry et al., "Newer Antiepileptic Drugs: Gabapentin, Lamotrigine, Felbamate, Topirimate, and Fosphenytoin," American Family Physician 57(3): 513-520 (1998).

Devinsky et al., "New Antiepileptic Drugs for Children: Felbamate, Gabapentin, Lamotrigine, and Vigabatrin," Journal of Child Neurology 9 (Suppl. 1): S33-S45 (1994).

Eckhardt et al., "Gabapentin Enhances the Analgesic Effect of Morphine in Healthy Volunteers," Anesth. Analg. 91: 185-91 (2000).

Eldon et al., "Lack of Effect of Gabapentin on the Pharmacokinetics of a Norethindrone Acetate/Ethinyl Estradiol-Containing Oral Contraceptive," *Neurology*, 43, A307 (1993) (579P).

Elger et al., "New Antiepileptic Drugs in Epileptology," *Neuropsychobiology* 38: 145-48 (1998).

Elwes et al., "Clinical Pharmacokinetics of Newer Antiepileptic Drugs," *Clin. Pharmacokinet.* 30(6): 403-415 (1996).

Emilien et al., "Pharmacological Management of Epilepsy, Mechanism of Action, Pharmacokinetic Drug Interactions, and New Drug Discovery Possibilities," *International Journal of Clinical Pharmacology and Therapeutics* 36(4): 181-194 (1998).

Ferrier, "Lamotrigine and Gabapentin: Alternatives in the Treatment of Bipolar Disorder," Neuropsychobiology, 38: 192-197 (1998).

Fischer et al., "Lack of Serious Toxicity Following Gabapentin Overdose," *Neurology* 44 (May): 982-983 (1994).

Feely, "Clinical Review: Drug Treatment of Epilepsy," *BMJ* 318: 1069 (1999).

Freeman et al., "Mood Stabilizer Combinations: A Review of Safety and Efficacy," *American J. Psychiatry* 155(1): 12-21 (1998).

Fromm "Gabapentin: Discussion," *Epilepsia* 25 (Suppl. 5): S77-S80 (1994).

Genton, "When Antiepileptic Drugs Aggravate Epilepsy," *Brain & Development* 22: 75-80 (2000).

Ghaemi et al., "Gabapentin Treatment of the Non-refractory Bipolar Spectrum: an Open Case Series," *Journal of Affective Disorders* 65: 167-171 (2001).

Gidal et al., "Gabapentin Absorption: Effect of Mixing with Foods of Varying Macronutrient Composition," *Annals of Pharmacotherapy* 32: 405-9 (1998).

Goa et al., "Gabapentin: A Review of its Pharmacological Properties and Clinical Potential in Epilepsy," *Drugs* 46(3): 409-427 (1993).

Gram, "Pharmacokinetics of New Antiepileptic Drugs," *Epilepsia* 37 (Suppl. 6): S12-S16 (1996).

Guberman, "Monotherapy or Polytherapy for Epilepsy?" *Canadian J. Neurol. Sci.* 25: S3-S8 (1998).

Handforth et al., "Efficacy and Tolerance of Long-Term, High-Dose Gabapentin: Additional Observations," *Epilepsia* 25(5): 1032-1037 (1994).

Hansen, "Treatment of Chronic Pain with Antiepileptic Drugs: A New Era," *Southern Medical Journal* 92(7): 642-649 (1999).

Johnston, "Gaba, Agonists as Targets for Drug Development," *Clinical and Experimental Pharmacology and Physiology* 19: 73-78 (1992).

Kälviäinen et al., "A Double-Blind Study of Gabapentin in Treatment of Partial Seizures," Epilepsia, 30(5): 661 (AES Proceedings, 1989).

Kelly, "Gabapentin Antiepileptic Mechanism of Action," *Neuropsychology* 38: 139-144 (1998).

Khurana et al., "Efficacy of Gabapentin Therapy in Children with Refractory Partial Seizures," *Journal of Pediatrics* 128: 829-33 (1996).

Kushnir et al., "Analysis of Gabapentin in Serum and Plasma by Solid-Phase Extraction and Gas Chromatography—Mass Spectrometry for Therapeutic Drug Monitoring," *Journal of Analytical Toxicology* 23: 1-6 (Jan./Feb. 1999).

Laird et al., "Use of Gabapentin in the Treatment of Neuropathic Pain," *Annals of Pharmacotherapy* 34: 802-7 (2000).

Leiderman et al., "Gabapentin as Add-on Therapy for Refractory Partial Epilepsy: Results of Five Placebo-Controlled Trials," *Epilepsia* 35(Suppl 5): S74-S76 (1994).

Letterman et al., "Gabapentin: A Review of Published Experience in the Treatment of Bi-polar Disorder and Other Psychiatric Conditions," *Pharmacotherapy* 19(5): 565-572 (1999).

Loiseau, "Treatment of Concomitant Illnesses in Patients Receiving Anticonvulsants: Drug Interactions of Clinical Significance," *Drug Safety* 19(6): 495-510 (1998).

MacDonald et al., "Antiepileptic Drug Mechanisms of Action," *Epilepsia* 34 (Suppl. 5): S1-S8 (1993).

Magnus, "Nonepileptic Uses of Gabapentin," Epilepsia, 40(Suppl. 6): S66-S72 (1999).

Mancardi et al., "Gabapentin is Effective in Treating Nocturnal Painful Tonic Spasmsin Multiple Sclerosis," *Neurology* 52(Suppl 2): A134 (Apr. 1999).

Mao et al., "Gabapentin in Pain Management," *Anesth Analg.* 91: 680-7 (2000).

Mathew et al., "Efficacy of Gabapentin in Migraine Prophylaxis," *Headache* 41: 119-128 (2001).

Mattson, "Antiepileptic Drug Monitoring: A Reappraisal," *Epilepsia* 36 (Suppl. 5): S22-S29 (1995).

Maurer et al., "Intestinal Absorption of Gabapentin in Rats," *Arzneim-Forsch/Drug Res.* 41(I), Nr. 2: 104-106 (1991).

McClean, "Gabapentin," *Epilepsia* 36 (Suppl. 2): S73-S86 (1995).

Meldrum, "Update on the Mechanism of Action of Antiepileptic Drugs," *Epilepsia* 37 (Suppl. 6): S4-S11 (1996).

Miles et al., "Variables Affecting the Intestinal Absorption of Water Soluble and Insoluble Antiepileptic Agents," *Pharmaceutical Research* 10(10 Suppl.): S223 (1993).

Miles et al., "Differentiating Possible Transport Mechanisms for the Intestinal Absorption of Gabapentin," *Pharmaceutical Research* 11(10 Suppl.): S365 (1994).

Morrell, "Epilepsy in Women: the Science of Why it is Special," *Neurology* 53(Suppl 1): S42-S48 (1999).

Morrell, "The New Antiepileptic Drugs and Women: Fertility, Reproductive Health, Pregnancy and Fetal Outcome," *Epilepsia* 37(Suppl. 6): S34-S44 (1996).

Morris "Gabapentin," *Epilepsia* 40 (Suppl. 5): S63-S70 (1999).

NDA 20-235 obtained via Freedom of Information Act, sections "Basic Pharmacokinetics Bioavailability"—optimal absorption, dose proportionality, and sustained release formulation (study #877-076), and "general comments to the medical reviewer", 1993.

Pande et al., "Treatment of Social Phobia with Gabapentin: A Placebo-Controlled Study," *Journal of Clinical Psychopharmacology* 19(4): 341-348 (1999).

Pande et al., "Placebo-Controlled Study of Gabapentin Treatment of Panic Disorder," *Journal of Clinical Psychopharmacology*, 20(4): 467-471 (2000).

Parks et al., "Practical Therapeutics: Drug Therapy for Epilepsy," *American Family Physician* 50(3): 639-648 (1994).

Patsalos et al., "Newer Antiepileptic Drugs: Towards and Improved Risk-Benefit Ratio," *Drug Safety* 11(1): 37-67 (1994).

Perucca, "The New Generation of Antiepileptic Drugs: Advantages and Disadvantages," *British Journal of Clinical Pharmacology* 42: 531-543 (1996).

Perucca et al., "Antiepileptic Drugs as a Cause of Worsening Seizures," *Epilepsia* 39(1): 5-17 (1998).

Raby, "Gabapentin Therapy for Cocaine Cravings," *Am J. Psychiatry* 157 (12): 2058-2059 (2000).

Ragucci et al., "Gabapentin-Induced Hypersensitivity Syndrome," *Clinical Neuropharmacology* 24(2): 103-105 (2001).

Riva et al., "Pharmacokinetic Interactions Between Antiepileptic Drugs: Clinical Considerations," *Clin. Pharmacokinetics* 31(6): 470-493 (Dec. 1996).

Rosenberg et al., "The Effect of Gabapentin on Neuropathic Pain," *Clinical Journal of Pain* 13(3): 251-255 (1997).

Rowan et al., "Intensive Monitoring and Pharmacokinetic Studies of Gabapentin in Patients with Generalized Spike-Wave Discharges," *Epilepsia* 30(5): 661 (AES Proceedings, 1989).

Sabers et al., "New Anticonvulsants: Comparative Review of Drug Interactions and Adverse Effects," *Drugs* 60(1): 23-33 (2000).

Salinsky et al., "Effects of Chronic Gabapentin and Carbamazepine Treatment on EEG, Alertness, and Cognition in Healthy Volunteers," *Epilepsia* 41 (Suppl. 7): 151 (2000, #2240).

Schmidt et al., "The New Anticonvulsant Drugs: Implications for Avoidance of Adverse Effects," *Drug Safety* 11(6): 422-431 (1994).

Shorvon et al., "Overview of the Safety of Newer Antiepileptic Drugs," *Epilepsia* 38 (Suppl 1): S45-S51 (1997).

Sindrup et al., "Efficacy of Pharmacological Treatments of Neuropathic Pain: An Update and Effect Related to Mechanism of Drug Action," *Pain* 83: 389-400 (1999).

Sivenius et al., "Double-Blind Study of Gabapentin in the Treatment of Partial Seizures," *Epilepsia* 32(4): 539-542 (1991).

Soliman et al., "Gabapentin Treatment for Cocaine Dependence in Methadone-Maintained Opiod-Dependent Patients," *Drug and Alcohol Dependence* 60(Suppl. 1): Abstracts, S208, 2000.

Stewart et al., "A Saturable Transport Mechanism in the Intestinal Absorption of Gabapentin is the Underlying Cause of the Lack of Proportionality Between Increasing Dose and Drug Levels in Plasma," *Pharmaceutical Research* 10(2): 276-281 (1993).

Thomson et al., "Pharmacokinetic Optimization of Anticonvulsant Therapy," *Clin. Pharmacokinet.* 23(3): 216-230 (1992).

Tomson et al., "Therapeutic Monitoring of the New Antiepileptic Drugs," *Eur. J. Clin. Pharmacol.* 55: 697-705 (2000).

Upton, "Mechanisms of Action of New Antiepileptic Drugs: Rational Design and Serendipitous Findings," *TiPS* 15: 456-463 (1994).

Vollmer et al., "Pharmacokinetics and Metabolism of Gabapentin in Rat, Dog, and Man," *Arzneim-Forsch./Drug Res.* 36(I), Nr. 5, 830-839 (1986).

Wang et al., "The Simultaneous Estimation of the Influx and Efflux Blood-Brain Barrier Permeabilities of Gabapentin Using a Microdialysis-Pharmacokinetic Approach," *Pharmaceutical Research* 13(3): 398-403 (1996).

White, "Comparative Anticonvulsant and Mechanistic Profile of the Established and Newer Antiepileptic Drugs," *Epilepsia* 40(Suppl. 5): S2-S10 (1999).

Wolf et al., "Gabapentin Toxicity in Children Manifesting as Behavioral Changes," *Epilepsia* 36(12): 1203-1205 (1996).

Wong et al., "Adverse Reactions to New Anticonvulsant Drugs," *Drug Safety* 23(1)35-56 (2000).

Wong et al., "Clinical Research: The Long-Term Use of Gabapentin, Lamotrigine, and Vigabatrin in Patients with Chronic Epilepsy," *Epilepsia* 40(1): 1439-1445 (1999).

Wong et al., "Disposition of Gabapentin in Anuric Subjects on Hemodialysis," *J. Clin. Pharmacol.* 35: 622-626 (1995).

Zylicz, "Painful Gynecomastia: An Unusual Toxicity of Gabapentin," *Letters*, 20(1): p. 2-3 (Jul. 2000).

Fara, J. "Physiological Limitations: Gastric Emptying and Transit of Dosage Forms" in Rate Control in Drug Therapy, L.F. Prescott, et al., Eds., Churchill Livingstone, New York (1985).

* cited by examiner

METHODS OF TREATMENT USING A GASTRIC RETAINED GABAPENTIN DOSAGE

BACKGROUND OF THE INVENTION

1. Technical Field

The present invention relates to the use of gabapentin in a gastric retained dosage form. More specifically, the invention relates to the use of such dosage form to treat epilepsy and other disease states.

2. Background

Gabapentin (1-(aminomethyl)cyclohexaneacetic acid) is an anti-epileptic drug that is currently available in 100 mg, 300 mg and 400 mg hard shell capsule as well as 600 mg and 800 mg tablet dosage forms, with recommended dosing of 900 mg to 1800 mg total daily dose in three divided dosages. The oral bioavailability is dose-dependent, with approximately 60% bioavailability for a dose in the range of 300-400 mg, but with only 35% bioavailability for a dose of 1600 mg (Bourgeois, *Epilepsia* 36 (Suppl. 5):S1-S7 (1995); Gram, *Epilepsia* 37 (Suppl. 6):S12-S16 (1996)). The decrease in bioavailability with dose has been attributed to carrier-mediated absorption (Stewart, et al., *Pharmaceutical Research* 10(2):276-281 (1993).

In early work with rats, Vollmer, et al., *Arzneim-Forsch/Drug Research* 36(1, Nr. 5):781-892 (1986) found that the absorption site for gabapentin was the duodenum. The absorption of gabapentin occurs relatively slowly with the peak plasma concentration occurring approximately 2-6 hours after dosing (Bourgeois, supra). The elimination of gabapentin is exclusively through renal pathways (Chadwick; *The Lancet* 343:89-91 (1994); Vollmer, supra; Thomson, et al., *Clin. Pharmacokinet.* 23(3):216-230 (1992); and Riva, et al., *Clin. Pharmacokinet.* 31(6):470-493 (1996)) with reported half-lives of 5-7 hours (Chadwick, supra) and 6-7 hours (Gram, supra).

A once- or twice-daily dosage form of gabapentin would be expected to improve compliance and therefore a controlled release dosage form has some distinct advantages over the conventional immediate release formulations. In addition, a controlled release dosage form would lower the maximum plasma concentration, and this may result in reduced side effects. Since gabapentin is absorbed high in the gastrointestinal tract, by means of a saturable transport mechanism, a gastric retained dosage form is particularly beneficial for delivery of gabapentin since the dosage form would be able to keep the drug in the region of absorption and show improved bioavailability by virtue of the slower release rate that avoids saturation of the carrier mediated transport of conventional dosages.

SUMMARY OF THE INVENTION

One aspect of the invention relates to a method of treating epilepsy comprising administering a therapeutically effective amount of gabapentin or a pharmaceutically acceptable salt thereof, in a gastric retained dosage form to a mammal in need of such treatment.

Yet another aspect of the invention relates to a method of treating neuropathic pain comprising administering a therapeutically effective amount of gabapentin or a pharmaceutically acceptable salt thereof, in a gastric retained dosage form to a mammal in need of such treatment.

Still another aspect of the invention relates to an improved method of administering a therapeutically effective amount of gabapentin to a patient in need thereof, the improvement comprising administering gabapentin or a pharmaceutically acceptable salt thereof, in a gastric retained dosage form.

DESCRIPTION OF THE INVENTION

Figure 1:
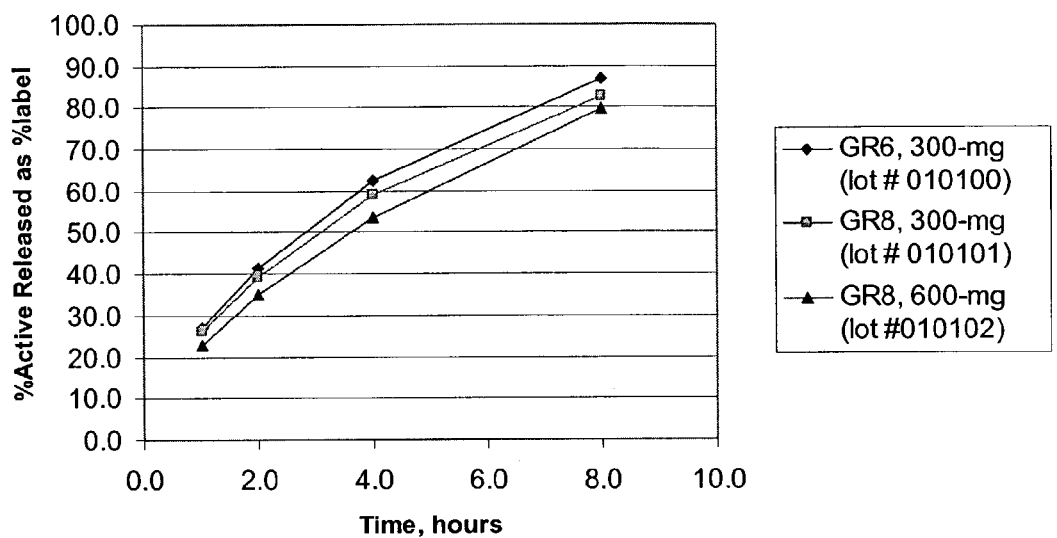
FIG. 1 illustrates the dissolution profiles for three GR™ formulations.

The invention relates to a method of treating a disease state, such as epilepsy, by administering gabapentin in a once- or twice-daily gastric retained dosage form. The gastric retained dosage form is particularly beneficial for delivery of gabapentin due to its prolonged transit in the upper gastrointestinal tract, which allows the drug to be absorbed adequately in the preferred region of absorption. In addition, a gastric retained dosage form increases the $t_{max}$ and allows for a smoother, more prolonged anti-spasmolytic effect. This dosage form also lowers the $C_{max}$ and may result in reduced incidence and/or severity of CNS side effects of the drug, such as somnolence, ataxia, fatigue and dizziness.

Method of Treatment

The instant invention is a method of treating a disease state comprising administering a therapeutically effective amount of gabapentin, or a pharmaceutically acceptable salt thereof, once- or twice-daily in a gastric retained dosage form to a mammal in need of such treatment. As used herein, the term "treating" covers treating the specified disease in a mammal, particularly a human, and includes:

(i) preventing the disease from occurring in a subject which may be predisposed to the disease but has not yet been diagnosed as having it;

(ii) inhibiting the disease, i.e. arresting its development; or (iii) relieving the disease, i.e. causing regression of the disease.

One embodiment of the invention relates to an improved method of administering a therapeutically effective amount of gabapentin to a patient in need thereof, the improvement comprising administering gabapentin or a pharmaceutically acceptable salt thereof, in a gastric retained dosage form.

Other embodiments of the invention relate to methods of treating specific disease states comprising administering a therapeutically effective amount of gabapentin or a pharmaceutically acceptable salt thereof, in a gastric retained dosage form to a mammal in need of such treatment. Such methods find utility in treating numerous disease states that are currently being treated with conventional immediate release formulations of gabapentin and include, by way of illustration and not limitation, epilepsy; neuropathic pain; psychiatric disorders such as bipolar disorder and panic disorder; movement disorders such as restless leg syndrome, periodic movement disorder of sleep, essential tremor and acquired nystagmus; and prophylaxis of migraine headaches.

The invention also contemplates administering one or more additional therapeutic agents with the gabapentin treatment. The selection of these additional therapeutic agents will depend upon the specific disease state being treated, and are described in detail below.

Active Ingredient

The active ingredient in the method of the invention is gabapentin. Gabapentin is preferably used in the free amphoteric form. Pharmaceutically acceptable salt forms that retain the biological effectiveness and properties of gabapentin and are not biologically or otherwise undesirable can also be used and may show superior bioavailability. As used herein, the term "gabapentin" is intended to include the agent itself, as well as its pharmaceutically acceptable salts.

Pharmaceutically acceptable salts may be amphoteric and may be present in the form of internal salts. Gabapentin may form acid addition salts and salts with bases. Exemplary acids that can be used to form such salts include, by way of example and not limitation, mineral acids such as hydrochloric, hydrobromic, sulfuric or phosphoric acid or organic acids such as organic sulfonic acids and organic carboxylic acids. Salts formed with inorganic bases include, for example, the sodium, potassium, lithium, ammonium, calcium, and magnesium salts. Salts derived from organic bases include, for example, the salts of primary, secondary and tertiary amines, substituted amines including naturally-occurring substituted amines, and cyclic amines, including isopropylamine, trimethylamine, diethylamine, triethylamine, tripropylamine, ethanolamine, 2-dimethyl aminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, fumarate, maleate, succinate, acetate and oxalate.

Additional Therapeutic Agents

The methods of the invention also contemplate the addition of one or more therapeutic agents with the gabapentin treatment.

For those embodiments of the invention where the gabapentin gastric retained dosage form is administered to treat epilepsy, such additional therapeutic agents can be other anti-epileptics or anticonvulsants, which include, by way of illustration and not limitation, hydantoins, iminostilbenes, valproates, phenyltriazines, barbiturates, deoxybarbiturates, benzodiazepines and carbamates. Such additional agents are preferably hydantoins, iminostilbenes, valproates or phenyltriazines.

The following examples of compounds within each of these classes is intended to be illustrative and not limiting in any manner. Examples of suitable hydantoin anticonvulsants include ethotoin, fosphenytoin, mephenytoin, and, preferably, phenytoin. An examples of a suitable iminostilbene is carbamazepine. Examples of suitable valproates include valprioic acid and sodium valproate. An exemplary suitable phenyltriazine is lamotrigene. A suitable barbiturate is phenobarbital and an exemplary deoxybarbiturate is primidone. An example of a suitable benzodiazepine is clorazepate. A suitable carbamate is felbamate.

For those embodiments of the invention where the gabapentin gastric retained dosage form is administered to treat neuropathic pain, such additional therapeutic agents can be selected from the group consisting of other anticonvulsants, tricyclic antidepressants, levadopa, and opioids.

The following examples of compounds within each of these classes is intended to be illustrative and not limiting in any manner. Examples of suitable anticonvulsants include carbamazepine, phenytoin and lamotrigine. Suitable tricyclic antidepressants include amitriptyline, imipramine, clomipramine and desipramine. Examples of suitable opioids include oxycodone and tramadol.

For those embodiments of the invention where the gabapentin gastric retained dosage form is administered to treat psychiatric disorders, such additional therapeutic agents can be selected from the group consisting of lithium, carbamazepine, valproate, trifluoperazine, clonazepam, risperidone, lorazepam, venlafaxine, clozapine, olanzapine, benzodiazepines, neuroleptics, tricyclic antidepressants, selective serontin reuptake inhibitor (SSRI's), buprupion, and nefadone.

For those embodiments of the invention where the gabapentin gastric retained dosage form is administered to treat bipolar disorder, such additional therapeutic agents can be selected from the group consisting of lithium, carbamazepine, valproate, trifluoperazine, clonazepam, risperidone, lorazepam, venlafaxine, clozapine, olanzapine, benzodiazepines, and neuroleptics.

For those embodiments of the invention where the gabapentin gastric retained dosage form is administered to treat depression, such additional therapeutic agents can be selected from the group consisting of tri-cyclic anti-depressants, SSRI's, bupropion, venlaxatine, and nefadone.

For those embodiments of the invention where the gabapentin gastric retained dosage form is administered to treat manic disorders, such additional therapeutic agents can be selected from the group consisting of diazepam, and oxazepam.

For those embodiments of the invention where the gabapentin gastric retained dosage form is administered to treat movement disorders, such additional therapeutic agents can be selected from the group consisting of benzodiazepines, dopaminergic agents, and opiates, particularly levodopa/carbidopa and clonazepam.

For those embodiments of the invention where the gabapentin gastric retained dosage form is administered for prophylactic treatment of migraine headaches, such additional therapeutic agents can be selected from the group consisting of tricyclic antidepressants (amitriptyline, doxepin, imipramine, maprotiline, protriptyline, desipramine), SSRI (fluoxetine), triptine (sumatriptan, etc.), and ergotamine.

Dosage

In general, the term "therapeutically effective amount" refers to that amount which is sufficient to effect treatment, when administered to a mammal in need of such treatment. The therapeutically effective amount will vary depending on the subject being treated, the severity of the disease state and the manner of administration, and may be determined routinely by one of ordinary skill in the art.

In particular, for use in the treatment of epilepsy or neuropathic pain with a gastric retained dosage form, gabapentin may be used at doses appropriate for treating epilepsy or neuropathic pain with immediate release dosage forms. However, the gastric retained dosage form is designed to provide for bioavailability of gabapentin at a level greater than or equal to 80% (>80%) relative to an equal dose of an immediate release dosage form. Typically, the method of the invention will involve administering gabapentin on a once- or twice-daily basis for as long as the condition persists.

An effective dosage of gabapentin for the treatment of epilepsy is typically in the range of about 300-3600 mg/day, typically about 900-2400 mg/day, more typically about 900-1800 mg/day.

An effective dosage of gabapentin for the treatment of neuropathic pain is typically in the range of about 100-4800 mg/day, typically about 300-3600 mg/day, more typically about 900-2400 mg/day.

An effective dosage of gabapentin for the treatment of psychiatric disorders is typically in the range of about 100-4800 mg/day, more typically about 900-3600 mg/day.

An effective dosage of gabapentin for the treatment of movement disorders is typically in the range of about 100-4000 mg/day, typically about 200-2700 mg/day, more typically about 500-2700 mg/day.

An effective dosage of gabapentin for the prophylactic treatment of migraine headaches is typically in the range of about 200-4000 mg/day, typically about 500-3600 mg/day, more typically about 900-2400 mg/day.

Dosage Regimen

The methods of the invention provide a once- or twice-daily dose of the gabapentin gastric retained dosage form. The dosage can be administered at any time, but it is preferred that the dosage is administered at the same approximate time each day and in approximately 12 hour intervals for the duration of treatment. In addition, it is preferred that the gastric retained dosage form be taken with food, for example with the morning or evening meals.

Accordingly, in one embodiment of the invention, gabapentin is administered once-daily, for example, in the morning (e.g., upon rising or with the morning meal) or in the evening (e.g., with the evening meal or near bedtime).

In another embodiment of the invention, gabapentin is administered twice-daily, for example, with the first dose being in the morning (e.g., upon rising or with the morning meal) and the second dose being in the evening (e.g., with the evening meal or near bedtime).

In another aspect of the invention, the method of administering a therapeutically effective amount of gabapentin in a gastric retained dosage form further includes administering one or more additional therapeutic agents.

The additional therapeutic agents can be administered at the same time or at a different time than the administration of gabapentin, and will depend upon the nature of the disease being treated as well as the agent itself. For example, when the additional agent is another anti-epileptic, a twice-daily dose is sufficient and it may be administered at the same time or at a different time than gabapentin. For purposes of facilitating patient compliance, administration of any of the aforementioned additional agents at the same time is preferred.

Dosage Form

There are several drug delivery systems that are suitable for use in delivering gabapentin in the method of the invention as they are particularly tailored to be gastric-retained dosages, such as the swellable bilayer described by Franz, et al., U.S. Pat. No. 5,232,704; the multi-layer tablet with a band described by Wong, et al., U.S. Pat. No. 6,120,803; the membrane sac and gas generating agent described in Sinnreich, U.S. Pat. No. 4,996,058; the swellable, hydrophilic polymer system described in Shell, et al., U.S. Pat. No. 5,972,389 and Shell, et al., WO 9855107; all of which are incorporated herein by reference.

Of particular interest are gastric retained dosage forms that contain hydrophilic polymers that swell to a size such that the dosage form is retained in the fed mode. For example, the gastric retained dosage form can contain polymers with a high swelling capacity such as polyethylene oxide, hydroxyethylcellulose and hydroxypropylmethylcellulose. The polymers are preferably of a moderate to high molecular weight ($4 \times 10^3$ to greater than $10^7$) to enhance swelling and provide control of the release of gabapentin. In one embodiment of the invention, a hydroxypropylmethylcellulose polymer of such molecular weight is utilized so that the viscosity of a 1% aqueous solution is about 4000 cps to greater than 100,000 cps. An example of suitable polyethylene oxide polymers are those having molecular weights (viscosity average) on the order of 2-7 million. A typical dosage form should swell to approximately 115% of its original volume within one hour after administration, and at a later time should swell to a volume that is 130% or more of the original volume. Fillers, binders, lubricants and other additives may also be included in the gastric retained dosage form, such as are well known to those of skill in the art.

A typical dosage form would provide for a drug delivery profile such that gabapentin both on an in vivo and in vitro basis, is delivered for at least 5 hours, and typically over a time period of about 8-10 hours. In order to provide for sustained delivery, it is preferable that at least 40 wt % of gabapentin is retained in the dosage form after 1 hour, i.e., no more than 60 wt % of the drug is administered in the first hour. In addition, it may be desired to utilize a dosage form that provides for substantially all of the gabapentin to be delivered over the intended duration, which is typically about 6-12 hours, where substantially all is taken to mean at least about 85 wt % of the gabapentin is administered.

In one embodiment of the invention, the gastric retained dosage form of gabapentin is a capsule dosage form that allows for the extended release of gabapentin in the stomach and comprises: (a) at least one component that expands on contact with gastric juice and contains an agent capable of releasing carbon dioxide or nitrogen, gabapentin or a pharmaceutically acceptable salt thereof; (b) at least one hydrophilic membrane in the form of a sachet which contains component (a), expands by inflation, floats on the aqueous phase in the stomach and is permeable to gastric juice and; (c) capsule dosage form which contains components (a) and (b) and which disintegrates without delay in the stomach under the action of gastric juice. Component (a) may also contain a pharmaceutically acceptable hydrophilic swelling agent such as lower alkyl ethers of cellulose, starches, water-soluble aliphatic or cyclic poly-N-vinylamides, polyvinyl alcohols, polyacrylates, polymethacrylates, polyethylene glycols and mixtures thereof, as well as other materials used in the manufacture of pharmaceutical dosage forms. Further details regarding an example of this type of dosage form can be found in Sinnreich, U.S. Pat. No. 4,996,058.

In another embodiment of the invention, the gastric retained dosage form of gabapentin is an extended release oral drug dosage form for releasing gabapentin into the stomach, duodenum and small intestine of a patient, and comprises: a single or a plurality of solid particles consisting of gabapentin or a pharmaceutically acceptable salt thereof dispersed within a polymer that (i) swells unrestrained dimensionally by imbibing water from gastric fluid to increase the size of the particles to promote gastric retention in the stomach of the patient in which the fed mode has been induced; (ii) gradually the gabapentin diffuses or the polymer erodes over a time period of hours, where the diffusion or erosion commences upon contact with the gastric fluid; and (iii) releases gabapentin to the stomach, duodenum and small intestine of the patient, as a result of the diffusion or polymeric erosion at a rate corresponding to the time period. Exemplary polymers include polyethylene oxides, alkyl substituted cellulose materials and combinations thereof, for example, high molecular weight polyethylene oxides and high molecular weight or viscosity hydroxypropylmethylcellulose materials. Further details regarding an example of this type of dosage form can be found in Shell, et al., U.S. Pat. No. 5,972,389 and Shell, et al., WO 9855107.

In yet another embodiment, a bi-layer tablet releases gabapentin to the upper gastrointestinal tract from an active containing layer, while the other layer is a swelling or floating layer. Details of this dosage may be found in Franz, et al., U.S. Pat. No. 5,232,704. This dosage form may be surrounded by a band of insoluble material as described by Wong, et al., U.S. Pat. No. 6,120,803.

Another embodiment of the invention uses a gastric retained swellable, sustained-release tablet having a matrix comprised of poly(ethylene oxide) and hydroxypropylmethylcellulose. This dosage form is illustrated in Example 1 and further details may be found in Gusler, et al., "Optimal Polymer Mixtures For Gastric Retentive Tablets," filed on like date herewith and identified as 10/029,134, the disclosure of which is incorporated herein by reference.

For those embodiments of the invention that include further administering additional therapeutic agents simultaneously with gabapentin, these agents can either be administered in the gastric retained dosage form that includes gabapentin or can be administered in a dosage form that is separate from gabapentin. Exemplary dosage forms are described below.

Dosage Form of Additional Agents

For those embodiments of the invention that include further administering one or more additional therapeutic agents, such dosages can be any suitable formulation as are well known in the art. For those additional agents where controlled release is desirable, the agent may be incorporated in the gabapentin gastric retained dosage form or be administered in a separate gastric retained or other controlled release formulation dosage form. For those additional agents where immediate release is desirable, the agent may be incorporated in a coating around the gabapentin gastric retained dosage form or in a separate layer of a bilayer tablet, the agent may be simply enclosed in the capsule of the aforementioned gabapentin gastric retained capsule dosage form, or the agent may be administered in a separate immediate release dosage form.

Typically, dosage forms contain the additional agent (another anti-epileptic or anticonvulsant agent) in combination with one or more pharmaceutically acceptable ingredients. The carrier may be in the form of a solid, semi-solid or liquid diluent, or a capsule. Usually the amount of active agent is about 0.1-95 wt %, more typically about 1-50 wt %. Actual methods of preparing such dosage forms are known, or will be apparent, to those skilled in this art; for example, see *Remington's Pharmaceutical Sciences*, Mack Publishing Company, Easton, Pa., 18th Edition, 1990. The dosage form to be administered will, in any event, contain a quantity of the additional therapeutic agent(s) in an amount effective to alleviate the symptoms of the subject being treated.

In the preparation of pharmaceutical formulations containing the additional therapeutic agent in the form of dosage units for oral administration the agent may be mixed with solid, powdered ingredients, such as lactose, microcrystalline cellulose, maltodextrin, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets such as chewable and oral disintegrating tablets.

Soft gelatin capsules may be prepared by mixing the active agent and vegetable oil, fat, or other suitable vehicle. Hard gelatin capsules may contain granules of the active agent, alone or in combination with solid powdered ingredients such as lactose, saccharose, sorbitol, mannitol, potato starch, corn starch, amylopectin, cellulose derivatives or gelatin.

Liquid preparations for oral administration may be prepared in the form of syrups or suspensions, e.g. solutions or suspensions containing about 0.2-20 wt % of the active agent and the remainder consisting of sugar or sugar alcohols and a mixture of ethanol, water, glycerol, propylene glycol and polyethylene glycol. If desired, such liquid preparations may contain coloring agents, flavoring agents, saccharin and carboxymethyl cellulose or other thickening agents. Liquid preparations for oral administration may also be prepared in the form of a dry powder to be reconstituted with a suitable solvent prior to use.

When the method of the invention includes administering another anti-epileptic or an anticonvulsant agent, there are numerous commercially available dosage forms that can be administered. In addition, other formulations can be readily designed based upon knowledge in the art, and include the gastric-retained delivery systems described above.

Typical dosage forms of the other anti-epileptics or anticonvulsants suitable for use in the invention include tablets, capsules, oral suspensions and syrup. One of skill in the art can readily prepare one of these exemplary formulations or the other anti-epileptic can be administered by means of one of the numerous commercially available products, examples of which are provided below.

Commercially available hydantoin anticonvulsants include, for example, Peganone® (ethotoin, Abbott); Mesantoin® (mephenytoin, Sandoz); and Dilantin® (phenytoin, Warner-Lambert).

Typical dosage forms of the antineuralgics suitable for use in the invention include tablets, capsules and oral suspensions. One of skill in the art can readily prepare one of these exemplary formulations or the antineuralgic can be administered by means of one of the numerous commercially available products, examples of which are provided below.

Commercially available antineuralgics include, for example, Atretol® (carbamazepine, Elan).

Although specific examples of suitable anti-epileptic, anticonvulsant agent and antineuralgic formulations are described above, it is understood that the invention is not limited to those examples as there are numerous other formulations that can be used to deliver the other anti-epileptic or anticonvulsant agents.

The general methods of the invention are best understood with reference to the following examples which are intended to enable those skilled in the art to more clearly understand and to practice the present invention. These examples are not intended, nor are they to be construed, as limiting the scope of the invention, but are merely illustrative and representative thereof.

EXAMPLE 1

Tablets were manufactured using a dry blend process, and hand made on a Carver 'Auto C' Press (Fred Carver, Inc., Indiana). The dry blend process consisted of blending all of the ingredients in a plastic bag, and compressing into a 1000 mg tablet (600 mg gabapentin dose) using a 0.7086"×0.3937" Mod Oval die (Natoli Engineering). The parameters for the operation of the Carver 'Auto C' Press were as follows: 4000 lbs. force, 0 second dwell time (the setting on the Carver Press), and 100% pump speed.

| | Formulation Composition (wt %) | | | |
|---|---|---|---|---|
| Sample # | Active | PEO Coagulant | Methocel K100M | M. St. |
| 1 | 60.0 | 39.0 | 0.0 | 1 |
| 2 | 60.0 | 24.3 | 14.7 | 1 |
| 3 | 60.0 | 0.0 | 39.0 | 1 | where:
Active = gabapentin
PEO Coagulant = poly(ethylene oxide), grade PolyOx Coagulant, NF FP grade, manufactured by Union Carbide/Dow Chemical Company
Methocel K100M = hydroxypropylmethylcellulose, grade Methocel K100M, premium, manufactured by Dow Chemical Company
M. St. = magnesium stearate, NF, supplied by Spectrum Chemical Company The dissolution was determined in USP apparatus 1 (40 mesh baskets), 100 rpm, in deionized water. Samples, 5 ml at each time-point, were taken without media replacement at 1, 4 and 8 hours.

The resulting cumulative dissolution profile, based upon a theoretical percent active added to the formulations is presented in tabulated form below:

| | Theoretical wt % of Active Released | | |
|---|---|---|---|
| Time (hours) | Sample 1 | Sample 2 | Sample 3 |
| 1 | 15.4 | 14.8 | 18.6 |
| 4 | 39.4 | 37.4 | 43.3 |
| 8 | 61.7 | 57.8 | 64.7 |

EXAMPLE 2

Tablets were manufactured using a dry blend process, and hand made on a Carver 'Auto C' Press (Fred Carver, Inc., Indiana). The dry blend process consisted of blending all of the ingredients in a plastic bag, and compressing into a 600 mg tablet (300 mg gabapentin) using a 0.6299"×0.3937" Mod Oval die (Natoli Engineering). The parameters for the operation of the Carver 'Auto C' Press were as follows: ~2000-2500 lbs. force, 0 second dwell time (the setting on the Carver Press), and 100% pump speed.

| | Formulation Composition (wt %) | | | |
|---|---|---|---|---|
| Sample # | Active | PEO Coagulant | Methocel K15M | M. St. |
| 4 | 50.0 | 24.5 | 24.50 | 1 | where:
Active = gabapentin
PEO Coagulant = poly(ethylene oxide), grade PolyOx Coagulant, NF FP grade, manufactured by Union Carbide/Dow Chemical Company
Methocel K15M = hydroxypropylmethylcellulose, grade Methocel K15M, premium, manufacture by Dow Chemical Company
M. St. = magnesium stearate, NF, supplied by Spectrum Chemical Company The dissolution was determined in USP apparatus 1 (40 mesh baskets), 100 rpm, in deionized water. Samples, 5 ml at each time-point, were taken without media replacement at 1, 2, 4 and 8 hours. The resulting cumulative dissolution profile, based upon a theoretical percent active added to the formulation is presented in tabulated form below:

| Time (hours) | Theoretical wt % of Active Released Sample A |
|---|---|
| 1 | 20.6 |
| 2 | 32.4 |
| 4 | 49.7 |
| 6 | 63.1 |
| 8 | 74.0 |
| 10 | 82.6 |

EXAMPLE 3

Three Gstric Retentive (GR™) gabapentin formulas were manufactured utilizing a standard granulation technique. The formulations manufactured are shown in tabulated form below.

| Formulation for Clinical Trial Manufacture | | |
|---|---|---|
| Gabapentin GR8, 300-mg (GR8, 300-mg) | Gabapentin GR6, 300-mg (GR6, 300-mg) | Gabapentin GR8, 600-mg (GR8, 600-mg) |
| 44.76% Gabapentin | 44.76% Gabapentin | 61.11% Gabapentin |
| 21.99% Methocel ® K15M, premium | 16.46% Methocel ® K4M, premium | 7.59% Methocel ® K15M, premium |
| 21.99% Sentry ® PolyOx ® WSR Coagulant, NF FP | 21.99% Sentry ® PolyOx ® WSR 303, NF FP | 27.09% Sentry ® PolyOx ® WSR 303, NF FP |
| 7.49% Avicel ® PH-101, NF | 12.98% Avicel ® PH-101, NF | 0.00% Avicel ® PH-101, NF |
| 2.75% Methocel ® E5, prem. | 2.75% Methocel ® E5, prem. | 3.22% Methocel ® E5, prem. |
| 1.00% Magnesium Stearate, NF | 1.00% Magnesium Stearate, NF | 1.00% Magnesium Stearate, NF |
| 670-mg (Tablet weight) | 670-mg (Tablet weight) | 982-mg (Tablet weight) |
| 0.3937" × 0.6299" Mod Oval | 0.3937" × 0.6299" Mod Oval | 0.4062" × 0.75" Mod Cap |

Gabapentin was obtained from Plantex U.S.A. (Englewood Cliffs, N.J.). Methocel® brand hydroxypropyl methylcellulose (also known as hypromellose), and Sentry® PolyOx® brand polyethylene oxide were obtained from Dow Chemical (Midland, Mich.). Methocel E5, premium is a USP type 2910 hydroxypropyl methylcellulose with number average molecular weight of on the order of 6000-8000 and a viscosity of 5 cps as a 2% aqueous solution at 20 C. Methocel® K4M and Methocel® K15M are USP type 2208 hydroxypropyl methylcellulose with viscosities of 4000 cps and 15,000 cps, respectively, as a 2% aqueous solution at 20 C, and number average molecular weights on the order of 80,000 and 100,000, respectively. Sentry PolyOx® WSR 301, NF FP, Sentry® PolyOx® WSR Coagulant, NF FP and Sentry® PolyOx® WSR 303, NF FP have viscosity-average molecular weights of approximately 4,000,000, 5,000,000 and 7,000,000, respectively. Avicel PH-101, NF is microcrystalline cellulose supplied by FMC Corporation (Philadelphia, Pa.). Magnesium stearate, NF was supplied by Spectrum Quality Products (New Brunswick, N.J.).

The dissolution profiles, as determined by USP Apparatus I (100 rpm) in modified simulated gastric fluid, for three prototypes GR™ formulations are shown in FIG. 1.

EXAMPLE 4

Figure 2:
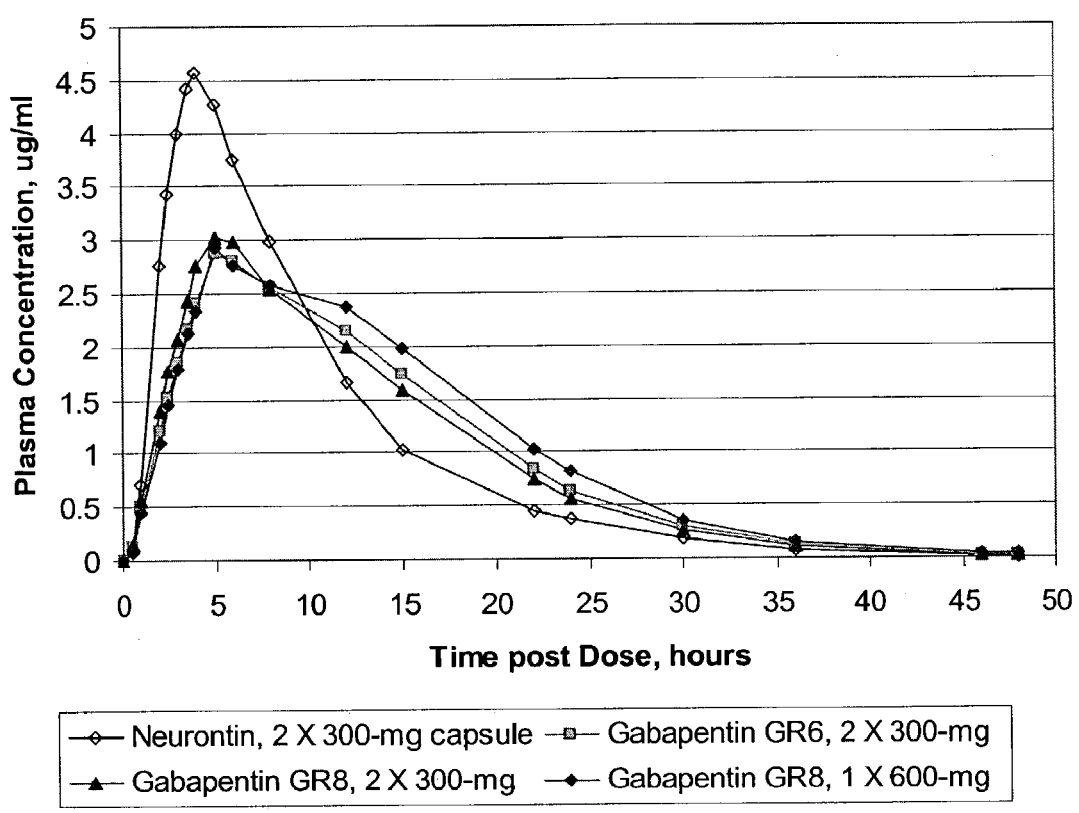
FIG. 2 illustrates the average plasma profile of three GR™ formulations and Nuerontin.

The pharmacokinetic profiles of the three formulations described in Example 3, administered as a 600-mg dose, were compared to Neurontin® immediate release 300-mg capsule in a randomized four-way cross-over experiment involving 15 healthy volunteers. Each subject was administered treatment of 600-mg gabapentin as one of the three GR™ formulations (1×600-mg tablet or 2×300-mg tablet) or Neurontin® capsules (2×300-mg) within 5 minutes of completing a high fat breakfast (FDA breakfast). Plasma samples were taken up to 48 hours post-dose. FIG. 2 illustrates the average plasma profile for the four treatments administered, and the pharmacokinetic data are summarized in tabulated form below.

Gabapentin Plasma Data - Average for 15 Subjects

| Dosing | | $AUC_{inf}^{\#}$ ((ug/ml)*hr) | $C_{max}^{\#}$ (ug/ml) | $T_{max}$ (hours) |
|---|---|---|---|---|
| Neurontin ®, 300-mg | Mean: | 46.65 | 4.72 | 3.93 |
| 2 × capsules | % CV: | 19.0 | 20.2 | 15.1 |
| GR6, 300-mg | Mean: | 44.43 | 2.97 | 6.63 |
| 2 × tablets | % CV: | 34.9 | 29.7 | 45.1 |
| GR8, 300-mg | Mean: | 41.84 | 3.10 | 5.63 |
| 2 × tablets | % CV: | 34.4 | 26.2 | 34.9 |
| GR8, 600-mg | Mean: | 48.01 | 3.13 | 7.13 |
| 1 × tablet | % CV: | 26.8 | 18.7 | 42.2 |

Geometric Mean and Geometric % CV are reported here

As demonstrated in FIG. 2 and in tabulated form above, GR™ formulations demonstrate sustained release with a lower maximum plasma concentration and a larger value for the time of the maximum concentration compared to the immediate release capsules without loss in the bioavailability as measured by the plasma $AUC_{inf}$.

Each of the patent applications, patents, publications, and other published documents mentioned or referred to in this specification is herein incorporated by reference in its entirety, to the same extent as if each individual patent application, patent, publication, and other published document was specifically and individually indicated to be incorporated by reference.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating epilepsy in a mammal comprising administering a therapeutically effective amount of a daily dosage of about 200 mg to about 4000 mg of gabapentin or a pharmaceutically acceptable salt thereof, dispersed in a gastric retained dosage form to the mammal in which a fed mode has been induced, wherein the dosage form comprises a single polymer matrix comprising at least one swellable hydrophilic polymer that swells in a dimensionally unrestrained manner by imbibing water to increase its size to promote gastric retention of the dosage form in the stomach of the mammal, and wherein upon contact with water, gabapentin is released by diffusion from the dosage form over a period of at least five hours and at least 40 wt % of the gabapentin is retained in the dosage form one hour after administration.

2. The method of claim 1 wherein the dosage form is administered once-daily.

3. The method of claim 2 wherein the dosage form is administered with a meal.

4. The method of claim 1 wherein the dosage form is administered twice-daily.

5. The method of claim 4 wherein each dosage form is administered with a meal.

6. The method of claim 1 which further comprises administering one or more additional anti-epileptics or anticonvulsants.

7. The method of claim 1 wherein the daily dosage is about 600-2700 mg.

8. The method of claim 1 wherein the daily dosage is about 900-1800 mg.

9. The method of claim 1 wherein the gastric retained dosage form releases gabapentin into the stomach, duodenum and small intestine.

10. The method of claim 1 wherein the dosage form provides administration of at least 80 wt % of the gabapentin to be delivered over a period of about 5-12 hours.

11. The method of claim 1, wherein the hydrophilic polymer is selected from the group consisting of polyethylene oxides, alkyl substituted cellulose materials, and combinations thereof.

12. The method of claim 1 wherein the dosage form further comprises a gas generating agent.

13. The method of claim 12 wherein the gabapentin is contained in a membrane sachet with the gas generating agent.

14. The method of claim 1 wherein the dosage form is a bilayered or multilayered adhesive tablet.

15. The method of claim 1 wherein the gastric retained dosage form is a capsule dosage form form that release gabapentin in the stomach,duodenum and small intestine.

16. The method of claim 1 wherein the gastric retained dosage form is a tablet and the matrix is comprised of poly (ethylene oxide) and hydroxypropylmethylcellulose.

17. A method of treating neuropathic pain in a mammal comprising administering a therapeutically effective amount of a daily dosage of about 100 mg to about 4800 mg of gabapentin or a pharmaceutically acceptable salt thereof, dispersed in a gastric retained dosage form to the mammal in which a fed mode has been induced, wherein the dosage form comprises a single polymer matrix comprising at least one swellable hydrophilic polymer that swells in a dimensionally unrestrained manner by imbibing water to increase its size to promote gastric retention of the dosage form in the stomach of the mammal, and wherein upon contact with water, gabapentin is released by diffusion from the dosage form over a period of at least five hours and at least 40 wt% of the gabapentin is retained in the dosage form one hour after administration.

18. The method of claim 17 wherein the dosage form is administered once-daily.

19. The method of claim 18 wherein the dosage form is administered with a meal.

20. The method of claim 17 wherein the dosage form is administered twice-daily.

21. The method of claim 20 wherein each dosage form is administered with a meal.

22. The method of claim 17 further comprising administering one or more therapeutic agents selected from the group consisting of anticonvulsants, tricyclic antidepressants, opioids, and levodopa.

23. The method of claim 17 wherein the daily dosage is about 300-3600 mg.

24. The method of claim 17 wherein the daily dosage is about 900-2400 mg.

25. The method of claim 17 wherein the gastric retained dosage form releases gabapentin to the stomach, duodenum and small intestine.

26. The method of claim 17 wherein the dosage form provides administration of at least 85 wt % of the gabapentin to be delivered over a period of about 5-12 hours.

27. The method of claim 1 wherein the hydrophilic polymer is selected from the group consisting of polyethylene oxides, alkyl substituted cellulose materials, and combinations thereof.

28. The method of claim 1 wherein the dosage form further comprises a gas generating agent.

29. The method of claim 28 wherein the gabapentin is contained in a membrane sachet with the gas generating agent.

30. The method of claim 17 wherein the dosage form is a bilayered or multilayered adhesive tablet.

31. The method of claim 17 wherein the dosage form is a capsule dosage form that releases gabapentin in the stomach duodenum and small intestine.

32. The method of claim 17 wherein the gastric retained dosage form is a tablet and the matrix is comprised of poly (ethylene oxide) and hydroxypropylmethylcellulose.

33. A method of administering a therapeutically effective amount of a daily dosage of about 100 mg to about 4800 mg of gabapentin to a mammal, comprising administering gabapentin or a pharmaceutically acceptable salt thereof, dispersed in a gastric retained dosage form to the mammal in which a fed mode has been induced and wherein the dosage form comprises a single polymer matrix comprising at least one swellable hydrophilic polymer that swells in a dimensionally unrestrained manner by imbibing water to increase its size to promote gastric retention of the dosage form in the stomach of the mammal, and wherein upon contact with water, gabapentin is released by diffusion from the dosage form over a period of at least five hours and at least 40 wt % of the gabapentin is retained in the dosage form one hour after administration.

34. The method of claim 33 wherein the dosage form is administered once-daily.

35. The method of claim 34 wherein the dosage form is administered with a meal.

36. The method of claim 33 wherein the dosage form is administered twice-daily.

37. The method of claim 36 wherein each dosage form is administered with a meal.

38. The method of claim 33 where the administering is to a mammal diagnosed with or suffering from epilepsy.

39. The method of claim 33 where the administering is to a mammal diagnosed with or suffering from neuropathic pain.

40. The method of claim 33 wherein the gastric retained dosage form releases gabapentin to the stomach, duodenum and small intestine.

41. The method of claim 33 wherein the dosage form provides administration of at least 80 wt % of the gabapentin to be delivered over a period of about 5-12 hours.

42. The method of claim 33 wherein the hydrophilic polymer is selected from the group consisting of polyethylene oxides, alkyl substituted cellulose materials, and combinations thereof.

43. The method of claim 33 wherein the dosage form further comprises a gas generating agent.

44. The method of claim 43 wherein the gabapentin is contained in a membrane sachet with the gas generating agent.

45. The method of claim 33 wherein the dosage form is a bilayered or multilayered adhesive tablet.

46. The method of claim 33 wherein the dosage form is a capsule dosage form that releases gabapentin in the stomach, duodenum and small intestine.

47. The method of claim 33 wherein the gastric retained dosage form is a tablet and the matrix is comprised of poly (ethylene oxide) and hydroxypropylmethylcellulose.

48. The method of claim 1, wherein the hydrophilic polymer swells to approximately 115% of its original volume within one hour of administration.

49. The method of claim 17, wherein the hydrophilic polymer swells to approximately 115% of its original volume within one hour of administration.

50. The method of claim 33, wherein the hydrophilic polymer swells to approximately 115% of its original volume within one hour of administration.

51. The method of claim 1, wherein the administering achieves a reduced incidence of side effects to the central nervous system, relative to a non-gastric retained dosage form.

52. The method of claim 17, wherein the administering achieves a reduced incidence of side effects to the central nervous system, relative to a non-gastric retained dosage form.

53. The method of claim 33, wherein the administering achieves a reduced incidence of side effects to the central nervous system, relative to a non-gastric retained dosage form.

54. The method of claim 1, wherein the hydrophilic polymer has a molecular weight of about $4\times10^3$ to about $1\times10^7$.

55. The method of claim 17, wherein the hydrophilic polymer has a molecular weight of about $4\times10^3$ to about $1\times10^7$.

56. The method of claim 33, wherein the hydrophilic polymer has a molecular weight of about $4\times10^3$ to about $1\times10^7$.

57. The method of claim 16, wherein the poly (ethylene oxide) has a molecular weight of about 2,000,000 daltons to about 7,000,000 daltons.

58. The method of claim 16, wherein the hydroxypropylmethylcellulose has a viscosity of about 4000 cps to about 100,000 cps as measured in a 1% aqueous solution.

59. The method of claim 41, wherein the hydroxypropylmethylcellulose has a viscosity of about 4000 cps to about 100,000 cps as measured in a 1% aqueous solution.

60. The method of claim 1, wherein the mammal is a human.

61. The method of claim 17, wherein the mammal is a human.

62. The method of claim 33, wherein the mammal is a human.

63. The method of claim 33, wherein the total amount of gabapentin in the daily dosage is about 300-3600 mg.

64. The method of claim 33, wherein the total amount of gabapentin in the daily dosage is about 900-2400 mg.

65. The method of claim 1, wherein the dosage form is a bilayered tablet.

66. The method of claim 17, wherein the dosage form is a bilayered tablet.

67. The method of claim 33, wherein the dosage form is a bilayered tablet.

* * * * *

UNITED STATES PATENT AND TRADEMARK OFFICE
CERTIFICATE OF CORRECTION

| | |
|---|---|
| PATENT NO. | : 7,438,927 B2 |
| APPLICATION NO. | : 10/280309 |
| DATED | : October 21, 2008 |
| INVENTOR(S) | : Brent Berner, Sui Yuen Eddie Hou and Gloria M. Gusler |

It is certified that error appears in the above-identified patent and that said Letters Patent is hereby corrected as shown below:

Title page: add --Related U.S. Application Data, Provisional Application No. 60/335,248 filed on October 25, 2001.--

Claim 28, line 1 thereof: change "The method of claim 1, wherein" to --The method of claim 17, wherein--

Claim 59, line 1 thereof: change "The method of claim 41, wherein" to --The method of claim 32, wherein--

Signed and Sealed this
Twenty-fifth Day of September, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,438,927 B2 | Page 1 of 1 |
| APPLICATION NO. | : 10/280309 | |
| DATED | : October 21, 2008 | |
| INVENTOR(S) | : Brent Berner, Sui Yuen Eddie Hou and Gloria M. Gusler | |

It is certified that error appears in the above-identified patent and that said Letters Patent is hereby corrected as shown below:

Title page: add --Related U.S. Application Data, Provisional Application No. 60/335,248 filed on October 25, 2001.--

Column 13, line 11 (Claim 28, line 1) thereof: change "The method of claim 1, wherein" to --The method of claim 17, wherein--

Column 14, line 45 (Claim 59, line 1) thereof: change "The method of claim 41, wherein" to --The method of claim 32, wherein--

This certificate supersedes the Certificate of Correction issued September 25, 2012.

Signed and Sealed this
Thirtieth Day of October, 2012

David J. Kappos
*Director of the United States Patent and Trademark Office*

UNITED STATES PATENT AND TRADEMARK OFFICE
CERTIFICATE OF CORRECTION

PATENT NO. : 7,438,927 B2  
APPLICATION NO. : 10/280309  
DATED : October 21, 2008  
INVENTOR(S) : Bret Berner, Sui Yuen Hou and Gloria M. Gusler It is certified that error appears in the above-identified patent and that said Letters Patent is hereby corrected as shown below:

Column 13, line 7 (Claim 27, line 1) thereof: change "The method of claim 1 wherein" to --The method of claim 17 wherein--.

Signed and Sealed this  
First Day of January, 2013

David J. Kappos  
*Director of the United States Patent and Trademark Office*